(12) United States Patent
Schuettler et al.

(10) Patent No.: US 12,144,651 B2
(45) Date of Patent: Nov. 19, 2024

(54) FLEXIBLE NEURAL ELECTRODE ARRAY

(71) Applicant: CorTec GmbH, Freiburg (DE)

(72) Inventors: Martin Schuettler, Emmendingen (DE); Juan Sebastian Ordonez, Ghent (BE); Tom Colin Bierbrauer, Freiburg (DE)

(73) Assignee: CorTec GmbH, Freiburg (DE)

( * ) Notice: Subject to any disclaimer, the term of this patent is extended or adjusted under 35 U.S.C. 154(b) by 0 days.

(21) Appl. No.: 18/196,909

(22) Filed: May 12, 2023

(65) Prior Publication Data

US 2023/0277137 A1 Sep. 7, 2023

Related U.S. Application Data

(62) Division of application No. 15/688,233, filed on Aug. 28, 2017, now Pat. No. 11,647,960.

(51) Int. Cl.
*A61B 5/00* (2006.01)
*A61B 5/24* (2021.01)
*A61B 5/291* (2021.01)
*A61N 1/05* (2006.01)

(52) U.S. Cl.
CPC .............. *A61B 5/6877* (2013.01); *A61B 5/24* (2021.01); *A61B 5/291* (2021.01); *A61N 1/0534* (2013.01); *A61N 1/0551* (2013.01); *A61N 1/0553* (2013.01); *A61N 1/0556* (2013.01); *A61B 2562/046* (2013.01); *A61B 2562/125* (2013.01); *A61B 2562/164* (2013.01)

(58) Field of Classification Search
CPC . A61B 5/6877; A61B 5/04001; A61B 5/0478; A61B 2562/046; A61B 2562/125; A61B 2562/164; A61N 1/0534; A61N 1/0551; A61N 1/0553; A61N 1/0556
See application file for complete search history.

(56) References Cited

U.S. PATENT DOCUMENTS 5,987,361 A * 11/1999 Mortimer ............. A61N 1/0556
607/152
2003/0040663 A1* 2/2003 Rule ...................... G01N 21/01
600/309

(Continued)

OTHER PUBLICATIONS

Non-Final Office Action issued for U.S. Appl. No. 15/688,233, mailed Sep. 24, 2020.

(Continued)

*Primary Examiner* — Adam Z Minchella
(74) *Attorney, Agent, or Firm* — Myers Wolin, LLC (57) ABSTRACT

A flexible neural electrode array is provided, comprising a layer of metal which is arranged on a first layer of polymeric material and which forms a number of contact pads. The first layer of polymeric material is flexible along a predefined direction, each contact pad of the number of contact pads having a sequence of cuts through the metal, each cut extending in a straight line across the predefined direction. Each cut has an inner end and an outer end, the inner end being within the contact pad, the outer end being at an edge of the contact pad, and each second cut of the sequence of cuts having its outer end at the same edge of the contact pad. A method is further provided for fabricating a flexible neural electrode array.

6 Claims, 6 Drawing Sheets

(56) References Cited

U.S. PATENT DOCUMENTS

| | | |
|---|---|---|
| 2004/0243204 A1* | 12/2004 | Maghribi ............. A61N 1/0551 607/115 |
| 2006/0003090 A1* | 1/2006 | Rodger ................ H05K 3/4682 427/96.8 |
| 2007/0123963 A1* | 5/2007 | Krulevitch ............... A61N 1/05 607/115 |
| 2008/0004673 A1* | 1/2008 | Rossing ................... A61N 1/05 607/44 |
| 2012/0051005 A1 | 3/2012 | Vanfleteran et al. |
| 2015/0065840 A1 | 3/2015 | Bailey |
| 2018/0068759 A1 | 3/2018 | Bihler |

OTHER PUBLICATIONS

Final Office Action issued for U.S. Appl. No. 15/688,233, mailed Jun. 9, 2021.
Notice of Allowance issued for U.S. Appl. No. 15/688,233, mailed Oct. 21, 2023.

* cited by examiner

Fig. 10

FLEXIBLE NEURAL ELECTRODE ARRAY

CROSS-REFERENCE TO RELATED APPLICATIONS

This application is a divisional application of U.S. patent application Ser. No. 15/688,233, filed Aug. 28, 2017, the entire contents of which are incorporated by reference herein.

FIELD OF INVENTION

The present invention relates to a flexible neural electrode array. The invention also relates to a technology of designing and producing mechanically very flexible neural electrode arrays. Neural electrode arrays are used for electrically interfacing with the nervous system in order to read biological signals or to electrically activate nervous tissue e.g., for diagnostic and/or therapeutic purposes.

BACKGROUND

State of the Art

Commonly, flexible neural electrode arrays consist of a flexible polymeric sheet in which metal electrode contacts are embedded. Above the electrode contacts, the polymeric sheet is spared so that metal contacts that provide the electrical interface to the nervous system are exposed.

While the polymeric sheet is usually made from soft silicone rubber, polyurethane or other elastomers with a thickness of some 10 µm up to 2 mm, the metal contacts are usually made from hard noble metal (alloy) foil of a few 10 µm thickness.

Problem Related to State of the Art

The stiffness of the metal contacts locally corrupts the mechanical flexibility of the polymeric sheet. Either it inhibits e.g. a tight bending radius or it is plastically deformed so that it would not be able to get back to its original shape once the bending is reversed. In case of combined bending and stretching, the metal contacts can actually angle off the sheet, exposing a metal edge that can potentially injure neural tissue.

SUMMARY

Embodiments of the invention relate to a flexible neural electrode array, comprising a layer of metal which is arranged on a first layer of polymeric material and which forms a number of contact pads, the first layer of polymeric material being flexible along a predefined direction, each contact pad of the number of contact pads having a sequence of cuts through the metal, each cut extending in a straight line across the predefined direction, wherein each cut having an inner end and an outer end, the inner end being within the contact pad, the outer end being at an edge of the contact pad, and each second cut of the sequence of cuts having its outer end at the same edge of the contact pad.

Advantageous embodiments of the invention may comprise the following features.

Each contact pad with the sequence of cuts forms at least one meander pattern portion when stretched in the predefined direction.

The electrode array may further comprise a second layer of polymeric material, the second layer of polymeric material being arranged at least partially on the layer of metal, and being flexible along the predefined direction, the second layer of polymeric material having at least one opening defining each contact of the number of contact pads.

This further layer may be applied for better fixating the metal layer.

The at least one meander pattern portion may be stretchable and/or compressible along the predefined direction.

The electrode array may further comprise a number of cut-aways arranged in the metal layer at the inner ends of the cuts.

The metal layer may further comprise a number of anchoring elements, the anchoring elements serving for fixating the metal layer with at least one of the layers of polymeric material.

The anchoring elements may be embodied as through holes in the metal layer, the holes being arranged in at least one predetermined region along the predefined direction, and holes allowing the polymeric layers to be connected to each other through the holes.

In one embodiment, at least one of the openings may be rectangular.

In one embodiment, at least one opening may be circular.

In one embodiment, at least one opening may have annular form.

Each cut of the sequence of cuts may extend radially with respect to the circular or annular form.

The electrode may be formed as cuff electrode, the at least one contact pads being ring-shaped.

The electrode may be formed as a cable, such as typical deep brain stimulation leads, with electrode contacts at an outer surface in shapes of rings or segmented rings.

Figure 6:
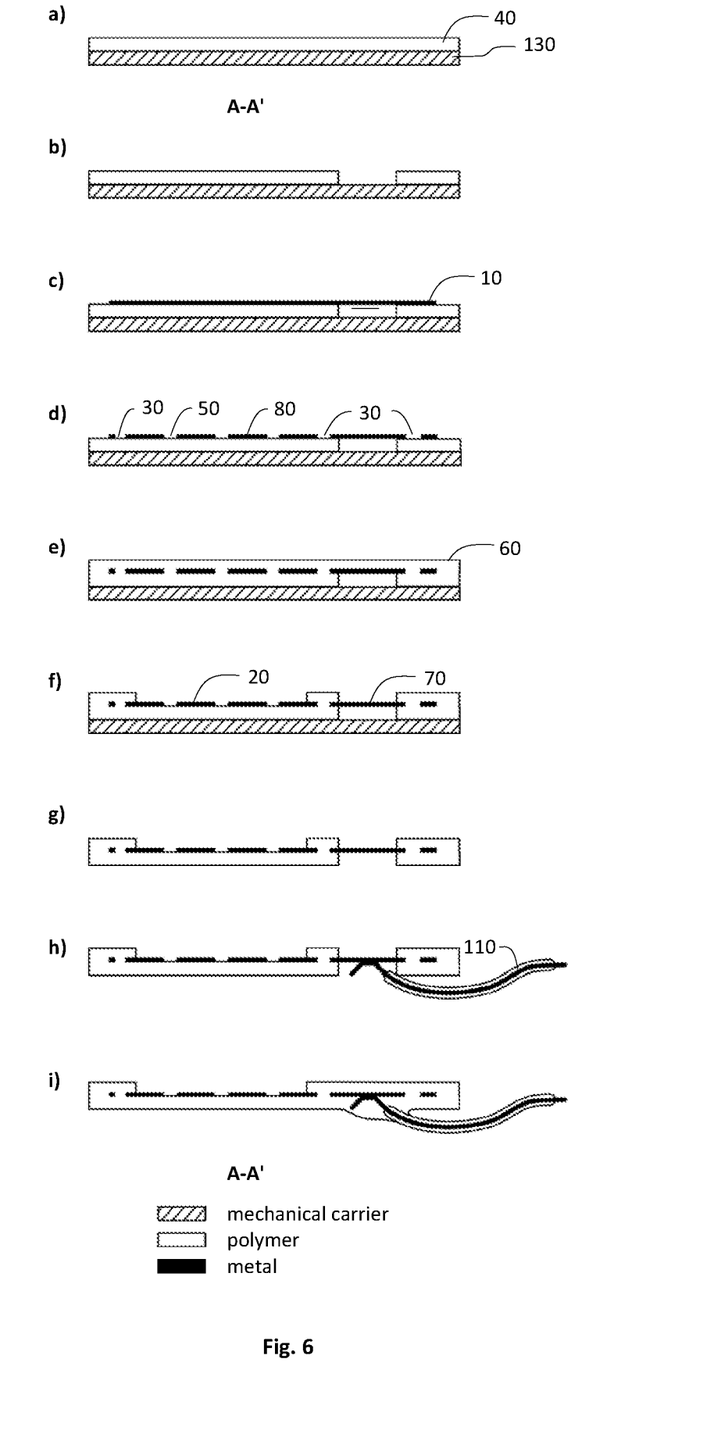
FIG. 6 illustrates a production process for the flexible neural electrode of the invention.

The invention further provides a method of fabricating a flexible neural electrode array, the method comprising the following steps:
  a) depositing a layer of polymer 40 on a mechanical carrier 130;
  b) removing the polymer layer, using a laser at location 70, from locations where weld contacts are to be formed;
  c) laminating a metal foil 10 on the polymer layer 40;
  d) cutting the metal foil 10 to shape with a laser, thus forming anchoring holes 30 and meander structures 80, 50;
  e) depositing a covering polymer layer;
  f) forming the weld contacts by ablating the polymer layer from the locations 70, and forming at least one electrode contact 20 by ablating the polymer 40 from at least one area of the polymer covering the metal layer.

The method may further comprise at least one of the following steps:
  g) removing the mechanical carrier 130;
  h) attaching a wire 110 to the weld pad 70; and
  i) sealing the weld 70 pad with polymer.

The layer of polymer may be deposited to a thickness of some 10 µm.

The metal foil may have a thickness of 5 to 50 µm.

In step e), the covering polymer layer may have a thickness of some 10 µm.

BRIEF DESCRIPTION OF THE DRAWINGS

The invention and embodiments thereof are described in connection with the drawing. In the drawing.

DETAILED DESCRIPTION

Figure 1:
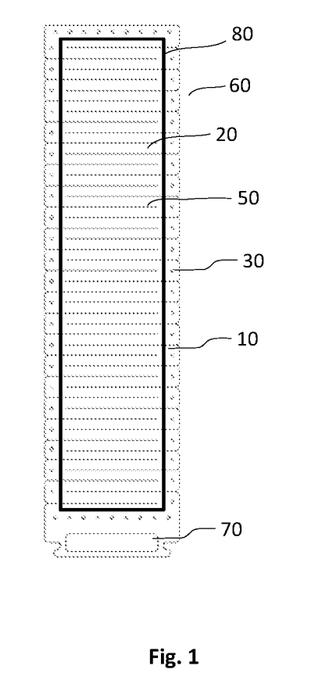
FIG. 1 is a top view on a flexible neural electrode according to an embodiment of the invention.
Figure 2:
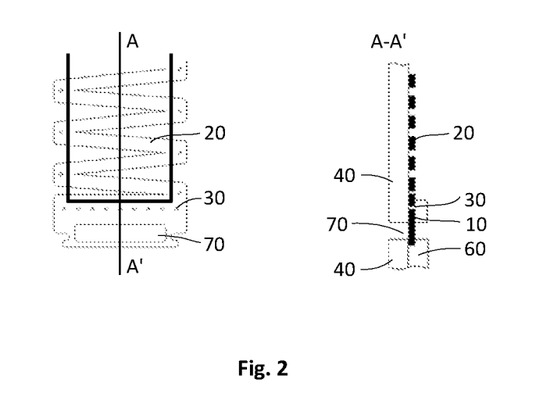
FIG. 2 is a detailed view on a sub section of the flexible neural electrode, the left portion being a top view while extended by pull-forces, the right portion being cross section A-A' of the left portion.

The flexible neural electrode array according to the first embodiment of the invention comprises a layer of at least one piece of metal foil 10, made from e.g., stainless steel, platinum, iridium, or platinum-iridium alloy, that is patterned to a meander, which extends in a longitudinal direction A-A' of the metal foil, refer to FIGS. 1 and 2. The basic shape of the piece of metal is rectangular. The piece of metal foil is sandwiched between a first (bottom) layer 40 and a second (top) layer 60, both of polymeric material, e.g., silicone rubber. The electrical contact intended for interfacing with the neural tissue is established by opening the second (top) polymer layer 60, thus exposing at least one part 20 of the metal foil 10. The at least one part 20 defines the one or more contact pads for interfacing with the neural tissue.

The outer edges along the direction A-A' of the meander are perforated, thus forming anchoring elements (through holes) 30, 30 so that first (bottom) polymer layer 40 and second (top) polymer layer 60 can reach through these holes 30 and mechanically fixate the metal 10, refer to FIG. 2. The resulting arrangement can follow stretching (refer to FIG. 3) and bending movements in longitudinal direction A-A'.

The creation of the meander can be done by straight cut lines 50 across direction A-A' (refer again to FIGS. 2, 3). These straight cut lines are also denoted as the sequence of cuts. Each cut goes through the metal layer. Each cut has its inner end within the contact pad, i.e., within the area of the contact pad, and its outer end at an outer edge of the contact pad, i.e., at the border of the area of the contact pad. Each second cut of the sequence of cuts has its outer end at the same edge of the contact pad, i.e., the each second cut end on the right edge of the contact pad, while the other cuts of the sequence of cuts end on the left edge of the contact pad.

Figure 3:
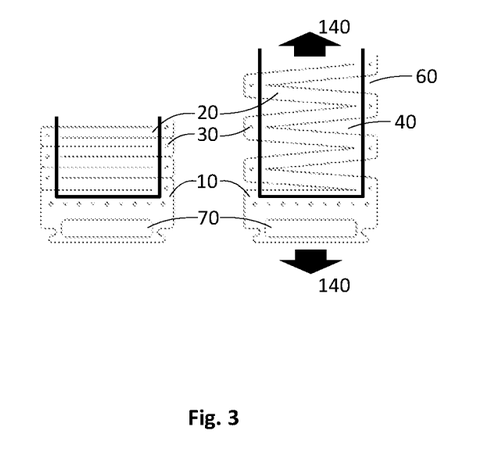
FIG. 3 is a detailed view on a sub section of flexible neural electrode; the left portion being relaxed (compact) and the right portion being extended by pull-forces.

In this embodiment, the cuts are parallel to each other, and orthogonal to the edges of the contact pad where they end.

Figure 4:
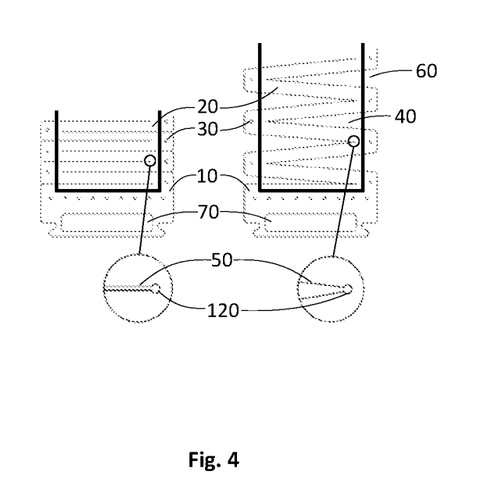
FIG. 4 is a detailed view of circular cut at the end of the meander cut lines, reducing mechanical stress peaks in the metal during contact stretching, as shown in the right illustration.

Additional to the cuts, circular cut-aways 120 at the ends of the cuts (refer to FIG. 4) can be done, allowing the mechanical stress on the metal during stretching to be more evenly distributed, thus lowering the risk of crack initiation.

As can be seen from FIG. 1, the at least one contact pad 20 is on the at least one meander pattern portion. The meander portion forms the contact pad, and provides the electrical interconnection between the contact pads as well. There is no need for a separate interconnection structure on the device.

For electrically connecting the electrode contact to a wire, the metal foil comprises a weld pad area 70 at a longitudinal end of the metal foil. The wire is attached to the metal contact at the weld pad area 70 e.g., by resistance welding, laser welding, ultrasonic welding, brazing or soldering. After attachment, the weld area is electrically sealed with a polymer.

Alternatively, the welding area may be located remote to the meander contact. The weld pad is electrically connected to the meander contact using a conductive path made from the same metal foil as the meander contact and the contact pad.

FIG. 2 is a detailed view on a sub section of the flexible neural electrode array, left: top view while extended by pull-forces; right: cross section A-A'. The meander pattern is formed by stretching the electrode array along predefined direction 140 (refer to FIG. 3). A-A' corresponds to the predefined direction 140.

As can be seen in FIG. 3, the electrode (i.e., the polymeric layers, and the patterned metal layer) is flexible along one predefined direction 140. The cuts 50 are across that predefined direction 140, refer to the left Figure. The cuts 50 enable the metal layer to be flexible along the predefined direction 140 too.

Figure 5:
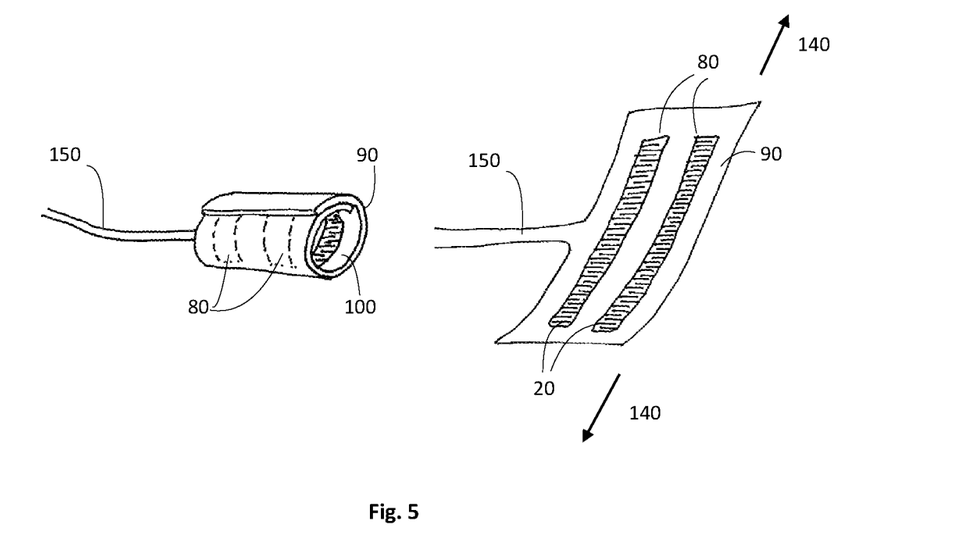
FIG. 5 is an illustration of a two-contact nerve cuff electrode to be wrapped around a peripheral nerve with two meander contacts embedded in a self-spiraling polymeric sheet forming 3-dimensional ring-shaped contacts, with the right portion being shown rolled in a cuff and the right portion being shown flattened.

An embodiment of a flexible electrode array is shown in FIG. 5. The flexible electrode array is a cuff electrode, which can be wrapped around a peripheral nerve. Hereto, it defines a volume 100 inside the cuff. The wrapping direction is along the direction 140. The cuff electrode has two meander contacts 80 embedded in a self-spiraling polymeric sheet 90. The cable 150 extends axially from the cuff.

The electrode array with the meander contact can be part of numerous applications. It is of particular use when a soft and flexible polymer body carries electrode contacts that experience stretching, bending, twisting.

The metal layer formed as a meander does not dominate the device's mechanical properties over that of the polymer layer(s).

Figure 7:
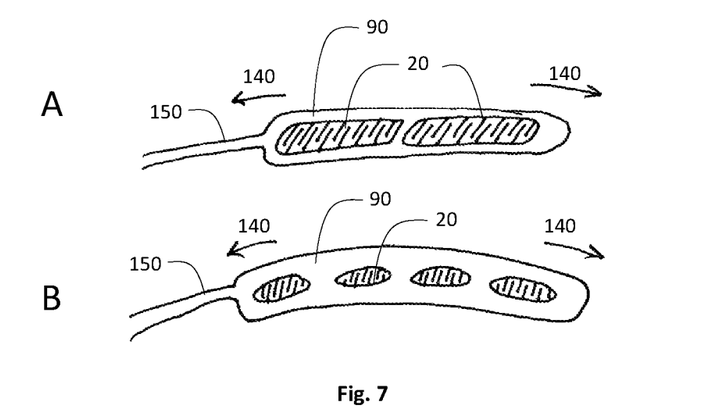
FIG. 7 illustrates in A) a paddle electrode with two strip-shaped meander contacts, and in B) a paddle electrode with four disk-shaped meander contacts.

FIG. 7 illustrates further embodiments of the invention. In FIG. 7A, a paddle electrode with two strip-shaped meander contacts is shown, and in FIG. 7B, a paddle electrode with four disk-shaped meander contacts 20 is shown. In the same way as in the first embodiment, the cuts in the metal layer are across the predefined direction 140 along which the electrode is flexible.

Figure 8:
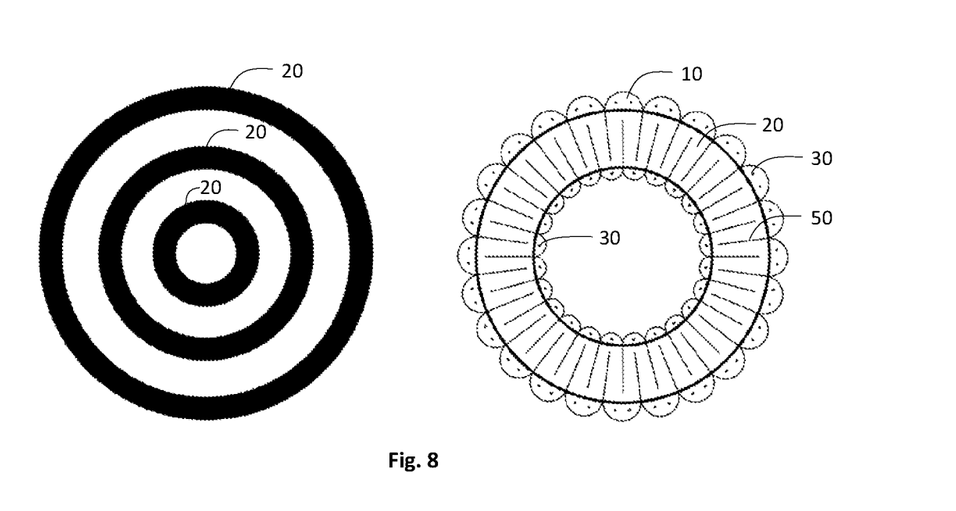
FIG. 8 illustrates how two-dimensional ring-shaped (annular) electrodes (example to the left: three concentric rings) can be realized as stretchable in two planar directions (including simultaneous stretching in x- and y-direction)

FIG. 8 illustrates a third embodiment of the invention. It illustrates how two-dimensional ring-shaped (annular) electrodes. In the example to the left: three concentric rings 20 can be realized as stretchable in two planar directions (including simultaneous stretching in planar x- and y-directions). The cuts in the pads 20 are not illustrated. The right sketch shows a single stretchable ring electrode can be designed applying meander contacts. Weld contacts for wires are not shown for clearness. Here, the cuts extend on lines which go out radially from the center. Each second cut of the sequence of cuts 50 ends on the outer perimeter of the pad 20. The other cuts end on the inner perimeter of the pad (i.e., the ring). As in the previously described embodiments, anchoring elements 30, i.e., through holes the metal along the edges of the pads.

Figure 9:
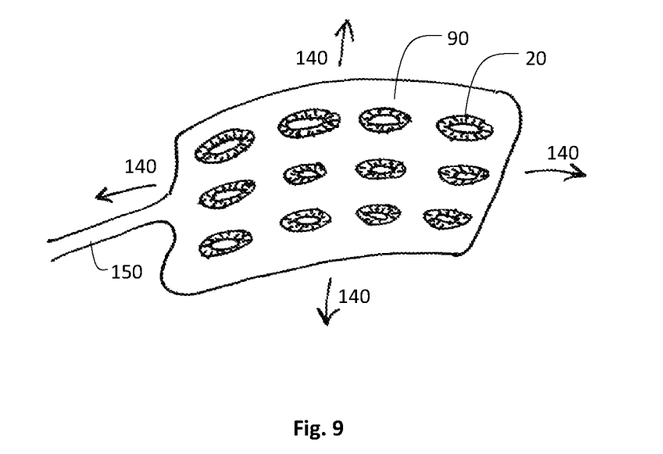
FIG. 9 illustrates a grid electrode with 12 ring-shaped (annular) electrode contacts e.g., of FIG. 8.

FIG. 9 illustrates a grid electrode with 12 ring-shaped (annular) electrode contacts. Each contact pad 20 is formed as described with reference to FIG. 8. A possible way of making meander ring-contacts is illustrated in FIG. 8 (right). The grid electrode of FIG. 9 is flexible along two planar directions 140 (x, y-directions), i.e., stretch forces 140 may be applied in the Figure left/right, and up/down.

Figure 10:
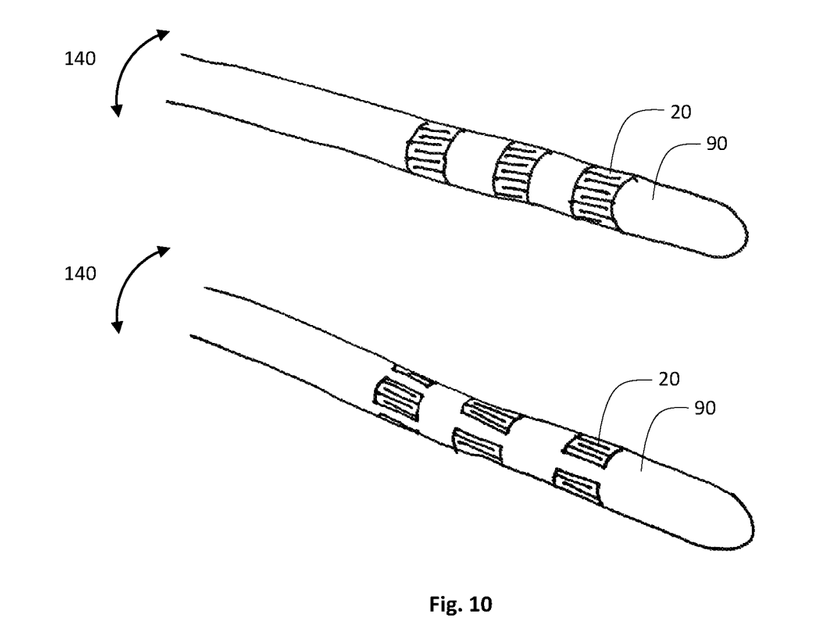
FIG. 10 illustrates a further embodiment of the invention in two views.

FIG. 10 illustrates a further embodiment of the invention. In this embodiment, the electrode is formed as a cable, such as typical deep brain stimulation leads, with electrode contacts 20 at an outer surface in shapes of e.g., three rings 20 (Fig above) or e.g., three segmented rings 20 (Fig bottom). Thus, the electrode (as illustrated in the right sketch of FIG. 5) is wrapped such that the pads 20 are at the outside surface of the thus formed cable. Since the metal is shaped as meanders, the electrode array (i.e., polymer layers 90 and metal layers 20) can be wrapped in the way as described. The predefined direction 140 is the direction of the wrapping.

Typical applications for the electrode of the invention include—but are not limited to—the contacts of
- nerve cuff electrodes with ring-shaped contacts, refer to FIG. 5;
- nerve cuff electrode with dot-shaped contacts;
- paddle or grid electrodes with areas of high mechanical bending/stretching/twisting forces, refer to FIG. 7.
- ring-shaped contacts, refer to FIG. 8, 9;
- ring-shaped contacts, on the outside of a cable-style electrode (such as a deep brain stimulation lead);
- segmented ring-shaped contacts, on the outside of a cable-style electrode (such as a segmented deep brain stimulation lead).

FIG. 6a) to i) illustrates a fabrication process suitable for producing the flexible electrode array of the invention.

In step a), a layer of polymer 40 is deposited to a thickness of typically some 10 μm on a mechanical carrier 130.

In step b) the polymer layer 40 is removed using a laser at location 70 where a weld contact is to be formed.

In step c), a metal foil 10 of a typical thickness of 5 to 50 μm is laminated on the polymer 40.

In step d), the metal foil 10 is cut to shape with a laser, forming anchoring holes 30 and the meander 80, 50.

In step e), a covering polymer layer 60 is deposited at a thickness of typically some 10 μm.

In step f) the polymer layer ablated at the locations of the weld contact 70 and the electrode contact 20.

In step g), the mechanical carrier 130 is removed.

In step h), a wire 110 is attached to the weld pad 70.

In step i), the weld 70 pad is sealed with polymer.

REFERENCE NUMERALS

10 Metal layer (foil)
20 Metal layer (contact pad(s))
30 Anchoring element (through hole)
40 First (bottom) layer of polymeric material
50 Cut (cutting edge of meander structure
60 Second (top) layer of polymeric material
70 Weld pad
80 Meander contact integrated in sheet
90 Polymeric sheet
100 Volume inside cuff for nerve placement
110 Wire
120 Circular cut-away as stress relieve
130 Mechanical carrier (fabrication aid)
140 direction of stretch force
150 Cable (wire bundle)
A-A' Longitudinal direction

The invention claimed is:

1. A method of fabricating a flexible neural cuff electrode array, the method comprising the following steps:
 a) depositing a layer of polymer on a mechanical carrier;
 b) removing the polymer layer, using a laser, from locations where weld contacts are to be formed;
 c) laminating a metal foil on the polymer layer;
 d) cutting the metal foil to shape with a laser, thus forming meander structures, the meander structures extending in a longitudinal direction of the metal foil and having outer edges along the longitudinal direction and straight inner edges across the longitudinal direction, each of the straight inner edges having one end at one of the outer edges and another end within the meander structure, perforating the outer edges of the meander structures with the laser thus forming anchoring holes in the meander structures, forming circular cut-aways at the inner ends of the straight inner edges of the meander structures, which are made from the metal foil;
 e) depositing a covering polymer layer such that the polymer layer reaches through the anchoring holes, and mechanically fixates the meander structures;
 f) forming the weld contacts by ablating the polymer layer from the locations, and forming at least one electrode contact by ablating the polymer from at least one area of the polymer covering the metal layer.

2. The method of claim 1, further comprising at least one of the following steps:
 g) removing the mechanical carrier;
 h) attaching a wire to the weld pad; and
 i) sealing the weld pad with polymer.

3. The method of claim 1, wherein in step a) the layer of polymer is deposited to a thickness of approximately 10 μm.

4. The method of claim 1, wherein the metal foil has a thickness of 5 to 50 μm.

5. The method of claim 1, wherein in step e), the covering polymer layer has a thickness of approximately 10 μm.

6. The method of claim 1, wherein the meander structures form exposed electrodes contacts.

* * * * *